US00PP29125P3

(12) United States Plant Patent
Brazelton et al.

(10) Patent No.: US PP29,125 P3
(45) Date of Patent: Mar. 20, 2018

(54) BLUEBERRY PLANT NAMED 'FCM12-131'

(50) Latin Name: ***Vaccinium corymbosum* hybrid**
Varietal Denomination: FCM12-131

(71) Applicant: Fall Creek Farm & Nursery, Inc., Lowell, OR (US)

(72) Inventors: David M. Brazelton, Walterville, OR (US); Adam L. Wagner, Eugene, OR (US); Peter Stefan Boches, Eugene, OR (US); Antonio A. Alamo Bermudo, Seville (ES)

(73) Assignee: Fall Creek Farm & Nursery, Inc., Lowell, OR (US)

( * ) Notice: Subject to any disclaimer, the term of this patent is extended or adjusted under 35 U.S.C. 154(b) by 0 days.

(21) Appl. No.: 15/330,667

(22) Filed: Oct. 25, 2016

(65) Prior Publication Data

US 2017/0118882 P1 Apr. 27, 2017

Related U.S. Application Data

(60) Provisional application No. 62/285,361, filed on Oct. 26, 2015.

(51) Int. Cl.
*A01H 5/08* (2006.01)

(52) U.S. Cl.
USPC ..... Plt./157

(58) Field of Classification Search
USPC ..... Plt./157
See application file for complete search history.

*Primary Examiner* — Annette H Para
(74) *Attorney, Agent, or Firm* — Hahn Loeser & Parks, LLP-San Diego

(57) ABSTRACT

The new blueberry plant variety 'FCM12-131' is provided. 'FCM12-131' is a commercial variety intended for the hand harvest fresh market. The variety is produced from a cross of 'ZF04-002' and 'FL95-138'. The new blueberry plant 'FCM12-131' as it grows in Tala, Mexico is distinguished by a dense, round growth habit, moderate vigor, closely spaced internodes, brightly colored salmon or orange new leaves, mature leaves that are glaucous, corollas that tend to be narrow and cylindrical or slightly urceolate in form, intense flowering and fruiting following pruning, and large fruit with a light blue color that is globose or slightly oblate in shape. The new blueberry plant 'FCM12-131' consistently produces larger fruit than the standard variety 'Biloxi', which is a very desirable characteristic.

7 Drawing Sheets

Latin name of the family, genus, and species:
Family—Ericaceae.
Genus—*Vaccinium.*
Species—*corymbosum* hybrid.
Variety denomination: The new blueberry plant claimed is of the variety denominated 'FCM12-131'.

STATEMENT REGARDING FEDERALLY-SPONSORED RESEARCH AND DEVELOPMENT

None.

BACKGROUND OF THE INVENTION

The present invention relates to the discovery of a new and distinct cultivar of southern highbush blueberry (*Vaccinium corymbosum* L. hybrid) plant, referred to as 'FCM12-131', as herein described and illustrated. The new blueberry plant variety 'FCM12-131' was selected near Colima, state of Colima, Mexico in 2012. 'FCM12-131' is a commercial variety intended for the hand harvest fresh market. The variety has medium vigor, ripens early and produces a large berry with good firmness, and a small picking scar on fruit derived from the current season's growth. 'FCM12-131' was selected for use in an evergreen production system in areas where zero effective chilling hours may be accumulated. The growing region of Colima, Mexico where 'FCM12-131' was originally selected is at a low latitude (~19.5° N) with a sub-tropical climate. In this region, temperatures rarely fall below 45° F. (the maximum temperature at which blueberry buds accumulate chill units to break dormancy) and day lengths only vary from between 10.8 hours in December to 13.2 hours in June. Under these conditions, many traditional low-chill blueberry varieties (developed in latitudes 25°-35°) do not produce flower buds or flowers. In the case of blueberry varieties that do flower under these conditions, the flowers are produced primarily on the current season's growth producing a structure that is often referred to as a 'primocane' inflorescence in the blueberry industry (although technically the word primocane refers specifically to a shoot on a bramble or caneberry). The 'primocane' inflorescences tend to be very elongated in form compared to an inflorescence produced at higher latitudes from dormant buds, and the primocane fruit often does not abscise well from the pedicel, resulting in a large picking scar which greatly limits shelf life. The blueberry industry in central Mexico is dominated by the variety 'Biloxi'. 'Biloxi' is one of the few traditional low chill varieties that grows well and produces fruit with a good picking scar in this growing environment. However, 'Biloxi' often produces an excessive proportion of small, unmarketable fruit. 'FCM12-131' was exceptional because it flowered and fruited more than most genotypes and also had large, firm fruit with a small picking scar. 'FCM12-131' also flowers very intensely after pruning, resulting in a shortened fruit harvest period relative to 'Biloxi'.

SUMMARY OF THE INVENTION

Pedigree and History: The new blueberry plant originated from a cross of 'ZF04-002' (female parent, unpatented) by 'FL95-138' (pollen parent, unpatented, owned by University of Florida and used with permission).

The cross that produced 'FCM12-131' (denominated by the cross code 'X09-101') was made in Lowell, Oreg., USA in 2009.

The new blueberry plant variety 'FCM12-131' was initially propagated by softwood cuttings in 2012. Rooted plants from these cuttings were field planted in Tala, Jalisco, Mexico and also shipped to Lowell, Oreg., USA in 2013. Additional plants have been propagated via softwood cuttings from the plants established in Tala, Mexico in 2014. The plants sent to Lowell, Oreg. were also propagated via softwood cuttings in 2014 and successfully used to establish in vitro culture lines in 2014.

The seedling family that produced 'FCM12-131' was initially grown in 50 cell propagation trays and shipped to Mexico in March, 2011 after the plants had reached sufficient size to be field planted. They were planted in a commercial blueberry field near Colima City, state of Colima, Mexico and evaluated for fruit production and quality beginning in December 2011. 'FCM12-131' was selected in 2012 because it flowered prolifically in a zero chill, evergreen production system and produced fruit with large size, firm texture, and a small picking scar. After being selected in Colima, 'FCM12-131' was propagated by softwood cuttings and a ten plant plot was established in Tala, Mexico (near Guadalajara). The ten plant plot was evaluated for fruit quality and yield in comparison to the standard varieties 'Biloxi' and 'Ventura' beginning in December, 2013. After two harvest seasons of evaluation, the yield and fruit quality of 'FCM12-131' were deemed sufficiently good to warrant launching it as a commercial variety.

The new blueberry plant 'FCM12-131' as it grows in Tala, Mexico is distinguished by a dense, round growth habit, moderate vigor, closely spaced internodes, brightly colored salmon or orange new leaves, mature leaves that are glaucous, corollas that tend to be narrow and cylindrical or slightly urceolate in form, intense flowering and fruiting following pruning, and large fruit with a light blue color that is globose or slightly oblate in shape. The new blueberry plant 'FCM12-131' consistently produces larger fruit than the standard variety 'Biloxi', which is a very desirable characteristic. The following characteristics of the new cultivar have been repeatedly observed and can be used to distinguish 'FCM12-131' as a unique *Vaccinium corymbosum* hybrid plant:

1) Globose or slightly oblate, light blue fruit that is significantly larger than fruit from the cultivar 'Biloxi'
2) Pink, salmon, or orange leaf color on new growth
3) Mature leaves glaucous with a blue green color
4) Narrow, often cylindrical corollas that may sometimes be urceolate or obovate in form
5) Small picking scar on fruit derived from the current season's growth
6) Intense flowering following pruning resulting in a shortened harvest period relative to the cultivar 'Biloxi' when grown under evergreen, zero chill production systems Plants of 'FCM12-131' propagated from softwood cuttings or in vitro are phenotypically stable and exhibit the same characteristics as the original plant. The parents 'ZF04-002' and 'FL95-138' have not been evaluated in the same environment of Mexico that 'FCM12-131' was selected in. However, in California, USA and Oregon, USA, 'ZF04-002' had corollas that were more urceolate in shape than 'FCM12-131'. Similarly, the blueberry plant 'FL95-138' grown in California, USA lacked salmon or orange coloration on new leaves compared to 'FCM12-131'. 'FCM12-131' also has leaves that are more glaucous than either 'ZF04-002' or 'FL95-138'.

DETAILED BOTANICAL DESCRIPTION

Figure 1:
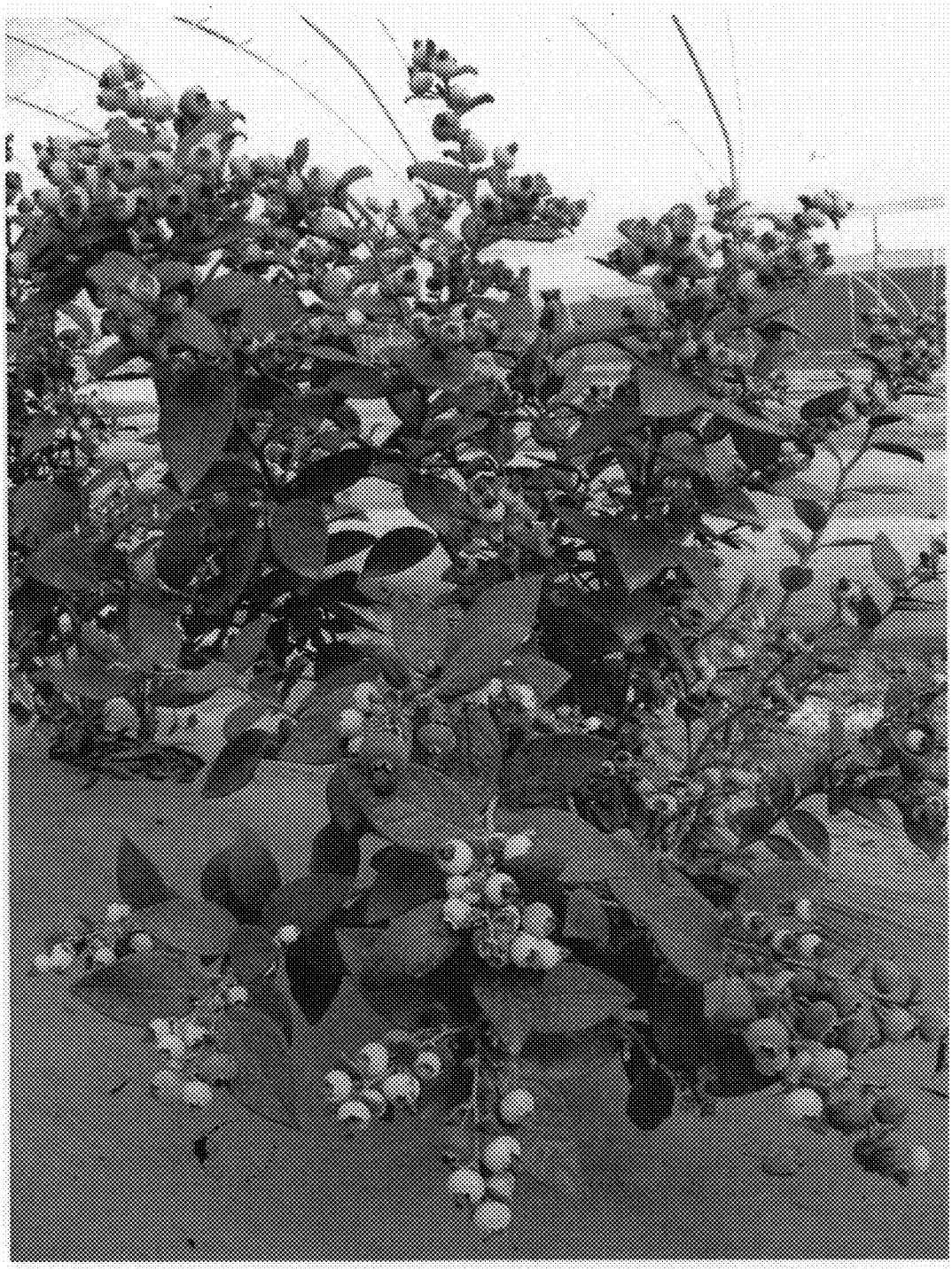
FIG. 1 is a photograph of a young plant (approximately 8 months after planting) of 'FCM12-131' grown in Tala, Mexico and photographed on Dec. 11, 2013 showing concentrated, precocious 'primocane' fruiting habit.
Figure 2:
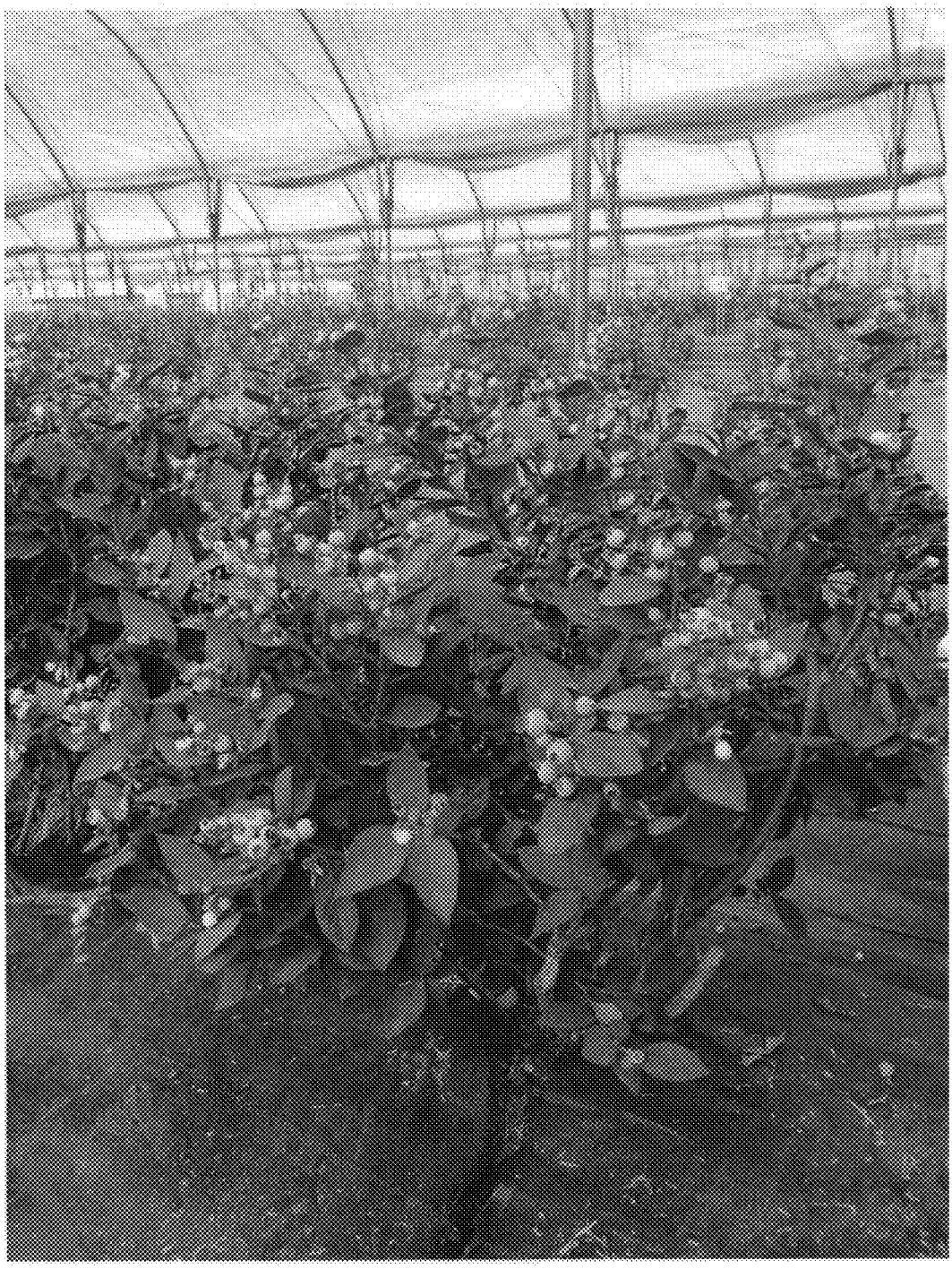
FIG. 2 is a photograph of a mature plant (approximately three years after planting) of FCM12-131 grown in Tala, Mexico and photographed on Dec. 7, 2015.
Figure 3:
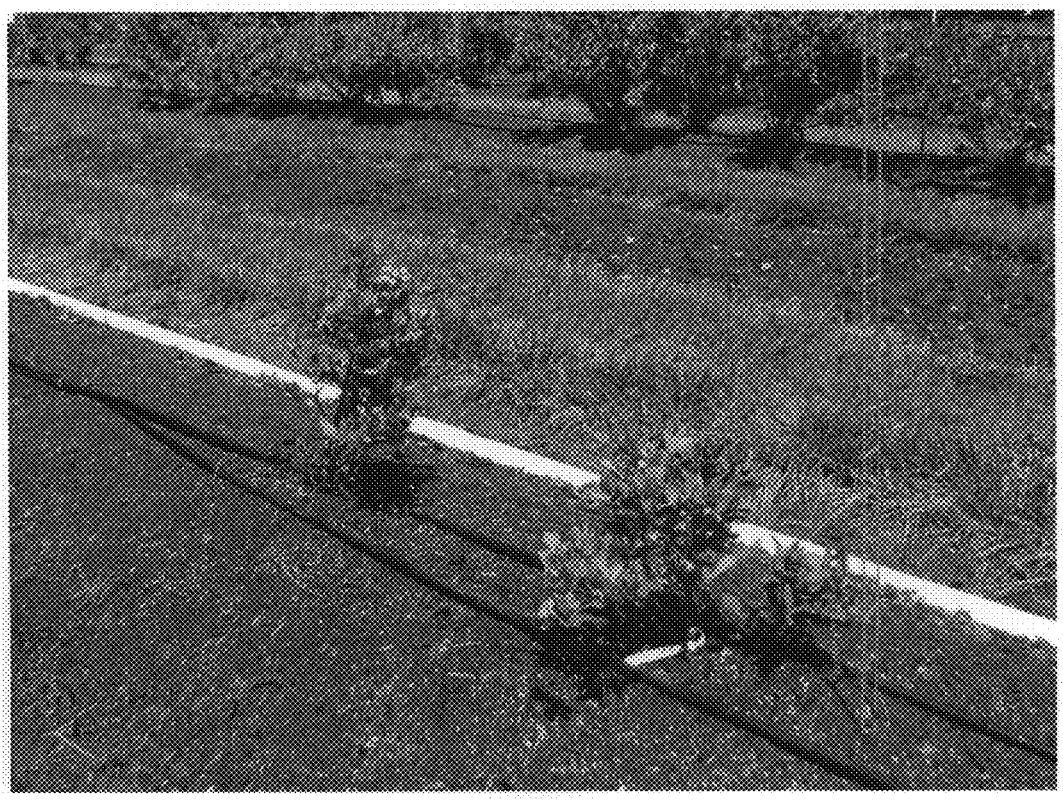
FIG. 3 is a photograph of a young plant of 'FCM12-131' grown in Lowell, Oreg. and photographed on Jun. 15, 2015, showing salmon and orange colored new growth.
Figure 4:
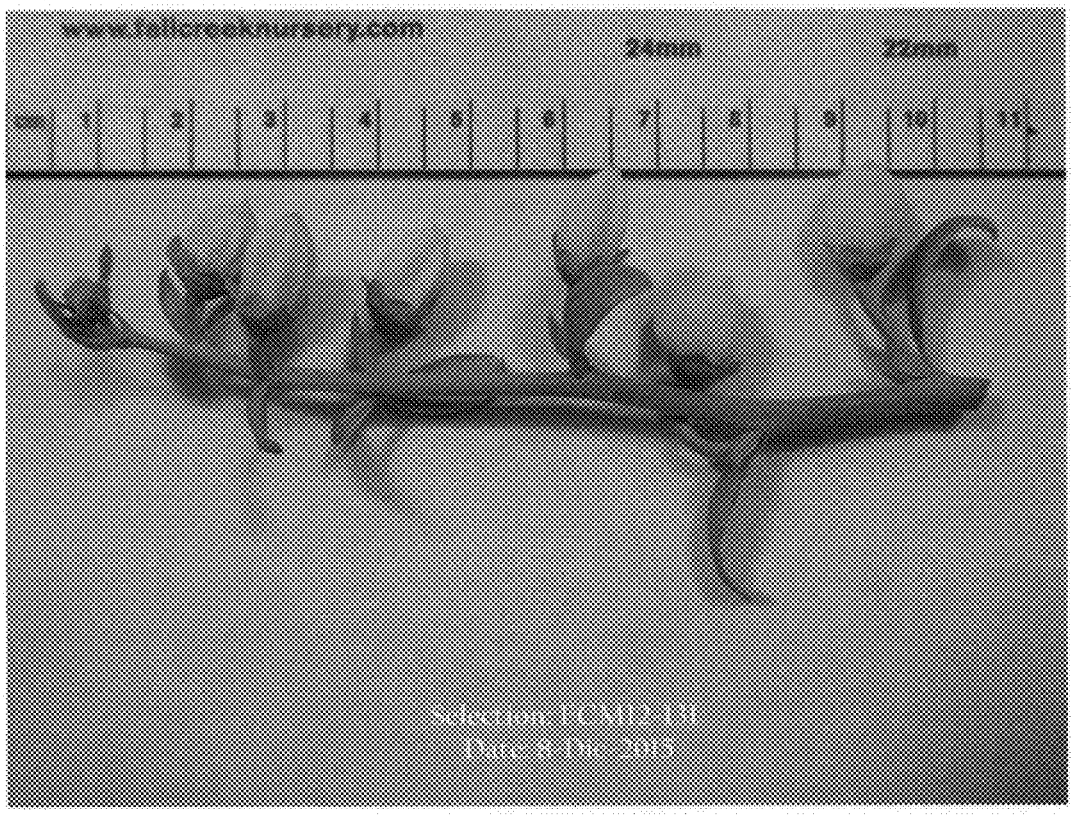
FIG. 4 is a photograph of flowers of 'FCM12-131' grown in Tala, Mexico and photographed on Dec. 8, 2015.
Figure 5:
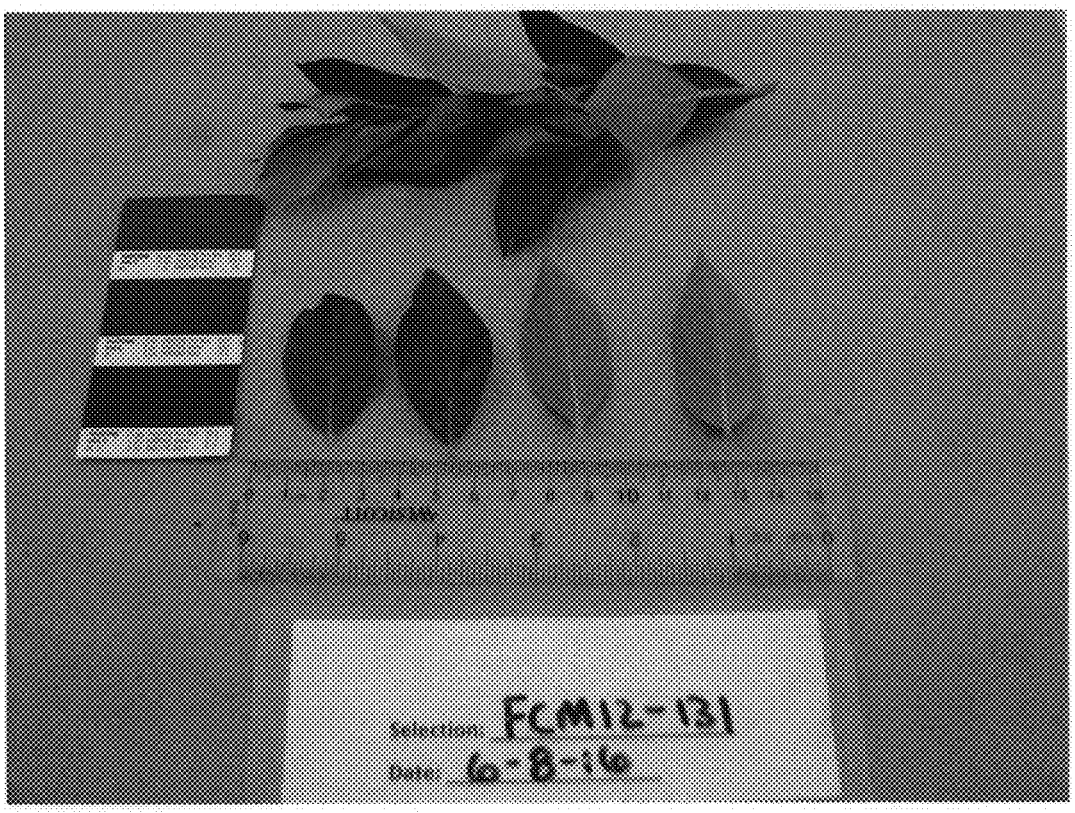
FIG. 5 is a photograph of leaves of 'FCM12-131' grown in Lowell, Oreg. and photographed on Jun. 16, 2016.
Figure 6:
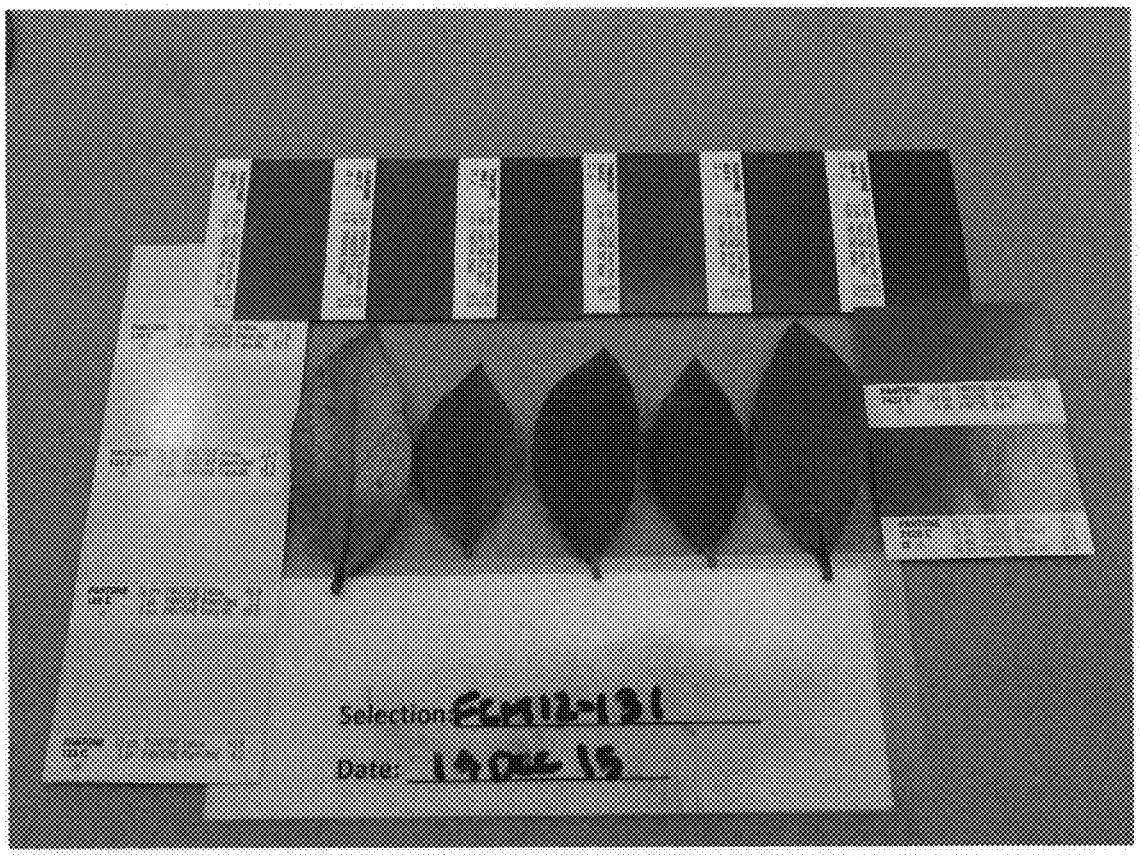
FIG. 6 is a photograph of leaves of 'FCM12-131' grown in Lowell, Oreg. and photographed on Dec. 15, 2015 showing fall color.
Figure 7:
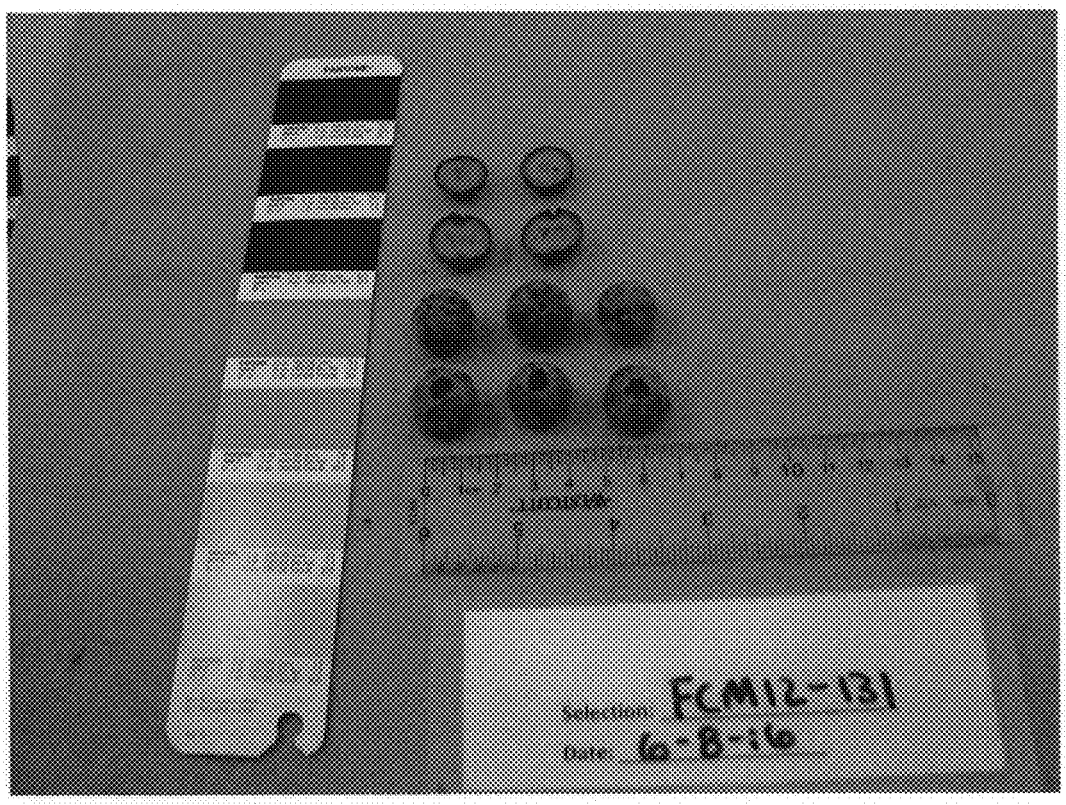
FIG. 7 is a photograph of fruit of 'FCM12-131' grown in Lowell, Oreg. and photographed on Jun. 8, 2016.

The following detailed description sets forth the distinctive characteristics of 'FCM12-131'. The data which defines these characteristics was collected from asexual reproductions of the original selection. Dimensions, sizes, colors, and other characteristics are approximations and averages set forth as accurately as possible. All measurements are the average of five observations. The plant history was taken on mature plants approximately 2 years of age, and the descriptions relate to plants grown in the field in Tala, state of Jalisco, Mexico unless otherwise noted (observations on fall leaf color and some other traits were collected on plants grown in Lowell, Oreg.). Descriptions of fruit characteristics were made on fruit grown in Tala, State of Jalisco, Mexico. Color designations are from "The Pantone Book of Color" (by Leatrice Eiseman and Lawrence Herbery, Harry N. Abrams, Inc., Publishers, New York 1990) unless noted otherwise. Where the Pantone color designations differ from the colors in the photographs, the Pantone colors are accurate.

VARIETY

Classification:

*a. Family.*—Ericaceae.

*b. Genus.*—*Vaccinium.*

*c. Species.*—*corymbosum* hybrid.

*d. Common name.*—Southern Highbush Blueberry.

Parentage:

*a. Female parent.*—'ZF04-002' (female parent, unpatented).

b. *Male parent*.—'FL95-138' (pollen parent, unpatented, owned by University of Florida and used with permission).

Market class: Commercial blueberry variety intended for the hand harvest fresh market.

PLANT

General:

a. *Parentage*.—'ZF04-002' (female parent, unpatented), 'FL95-138' (pollen parent, unpatented, owned by University of Florida and used with permission).
b. *Plant height*.—Average of 67.4 cm.
c. *Plant width*.—Average of 89.8 cm.
d. *Growth habit*.—Round or semi-erect.
e. *Growth*.—Moderately vigorous.
f. *Productivity*.—Good, average of 2.69 kilos per plant, per season on a 2 year old plant, compared to 1.86 kilos per plant, per season for the commercial variety 'Biloxi'.
g. *Cold hardiness*.—Not determined, likely USDA zone 7 given southern highbush parentage.
h. *Chilling requirement*.—Not determined, estimated at less than 700 hours less than 45 degrees Fahrenheit. Capable of fruiting well with zero chill hours when maintained in an evergreen state of growth.
i. *Leafing*.—Good leafing.
j. *Twigginess*.—Fairly twiggy.
k. *Resistance/susceptibility to root rot* (*phytopthora cinnamomii*).—Does not appear to be overly susceptible.
l. *Resistance/susceptibility to stem blight* (*botryosphaeria sp.*).—Does not appear to be overly susceptible.
m. *Resistance/susceptibility to phomopsis twig blight* (*phomopsis vaccinii*).—Not evaluated.
n. *Resistance/susceptibility to botrytis* (*botrytis cinerea*).—Does not appear to be overly susceptible.
o. *Resistance/susceptibility to leaf spot* (*septoria* spp.).—Does not appear to be overly susceptible.
p. *Resistance/susceptibility to leaf rust* (*naohidemyces vaccinii*).—Does not appear to be overly susceptible.
q. *Resistance/susceptibility to bud mites* (*acalatus vaccinii*).—Not evaluated.

STEM

General:

a. *Suckering tendency*.—Moderate.
b. *Mature cane color*.—Pantone Moss 16-0532.
c. *Mature cane length*.—Estimated at 50 cm.
d. *Mature cane width*.—Estimated at 50 mm.
e. *Bark texture*.—Rough.
f. *Fall color on new shoots*.—In Lowell, Oreg.: Pantone colors Barn Red 18-1531, Mineral Red 17-1537, Green Oasis 15-0538.
g. *Surface texture of new wood*.—Smooth.
h. *Internode length on strong, new shoots*.—Average of 8.21 mm.
i. *Average number of buds per fruiting lateral*.—Average of 3.6.

FOLIAGE

General:

a. *Time of beginning of leaf bud burst*.—Late February to mid-March in Lowell, Oreg.
b. *Leaf color* (*top side*).—Pantone Black Forest 19-0315.
c. *Leaf color* (*under side*).—Pantone Bluish Olive 18-0316.
d. *Leaf arrangement*.—Alternate.
e. *Leaf shape*.—Elliptic to lanceolate.
f. *Leaf margins*.—Entire.
g. *Leaf venation*.—Pinnate, anastomosing.
h. *Leaf apices*.—Acute.
i. *Leaf bases*.—Generally acute.
j. *Leaf length*.—Average of 62.77.
k. *Leaf width*.—Average of 34.63 mm.
l. *Leaf length/width ratio*.—1.81, moderately narrow.
m. *Leaf nectaries*.—Absent.
n. *Pubescence of upper side*.—Absent.
o. *Pubescence of lower side*.—Absent.
p. *Cross sectional profile*.—Revolute.
q. *Longitudinal profile*.—Frequently undulate.
r. *Attitude*.—Porrect.

Petioles:

a. *Length*.—Average of 3.40 mm.
b. *Width*.—Average of 1.85 mm.
c. *Color*.—Pantone Beechnut 14-0425.
d. *Surface texture*.—Smooth.

FLOWERS

General:

a. *Time of beginning of flowering*.—September 10 in Tala, Mexico. Mid-March in Lowell, Oreg.
b. *Time of* 50% *anthesis*.—Late March in Lowell, Oreg.
c. *Flower shape*.—Flowers from resting buds, such as observed in Lowell, Oreg., tend to be narrowly cylindrical or occasionally obovate (wider at the aperture end than base). Flowers from current season's growth on "primocanes" (such as those observed in Tala, Mexico) tend to be more urceolate.
d. *Flower fragrance*.—Faintly floral, rose.
e. *Immature flower color*.—In Tala, Mexico, Pantone Frozen Dew 13-0513. In Lowell, Oreg. immature flowers have more anthocyanin and match Pantone colors Dusty Cedar 18-1630, Peach Blossom 16-1626, and Snow White 11-0602.
f. *Pollen staining*.—Good, 95% fertile when stained with acetocarmine red.
g. *Self-compatibility*.—Good, 78% of self-pollinated flowers reached maturity.

Corolla:

a. *Color*.—Pantone Frozen Dew 13-0513.
b. *Length*.—Average of 9.86 mm.
c. *Width*.—Average of 9.65 mm.
d. *Aperture width*.—Average of 3.77 mm.
e. *Anthocyanin coloration of corolla at time of anthesis*.—Low.
f. *Corolla ridges*.—Not distinct.
g. *Protrusion of stigma*.—Average of 0.6 mm beyond lip of corolla.

Inflorescence:

a. *Length*.—Variable, average of 45.42 mm.
b. *Diameter*.—Average of 20.69 mm.

*c. Length of peduncle.*—Variable, average of 30.82 mm.
*d. Surface texture of peduncle.*—Smooth.
*e. Color of peduncle.*—Pantone Green Oasis 15-0538.
*f. Length of pedicel.*—Average of 9.87 mm.
*g. Surface texture of pedicel.*—Smooth.
*h. Color of pedicel.*—Pantone Green Banana 14-0434.
*i. Number of flowers per cluster.*—Average of 6.2.
*j. Flower cluster density.*—Loose.

Calyx (with sepals):
*a. Diameter.*—Average of 8.24 mm.
*b. Color (sepals).*—Pantone Tarragon 15-0326.
*c. Calyx surface.*—Smooth.

Stamen:
*a. Length.*—Average of 7.16 mm.
*b. Number per flower.*—10, occasionally 11. Average of 10.4.
*c. Filament color.*—Pantone Celery Green 13-0532.

Pistil:
*a. Length.*—Average of 9.30 mm.
*b. Ovary color (exterior).*—Pantone Leaf Green 15-0332.
*c. Style.*—Length — average of 10.86 mm.

Anther:
*a. Length.*—Average of 3.7 mm in Lowell, Oreg.
*b. Number.*—Average of 10 in Lowell, Oreg.
*c. Color.*—Pantone colors Baked Clay 18-1441 to Burnt Orange 16-1448 in Lowell, Oreg.

Pollen:
*a. Abundance.*—Moderate in Lowell, Oreg.
*b. Color.*—Pantone color Pale Banana 12-0824 in Lowell, Oreg.

FRUIT

General:
*a. Time of fruit ripening.*—Approximately October 30 in Tala, Mexico depending on timing of previous pruning.
*b. Time of 50% maturity.*—Approximately October November 15 in Tala, Mexico, depending on timing of previous pruning. In Lowell, Oreg. fruit ripens in mid-June.
*c. Fruit development period.*—Approximately 45 days.
*d. Mean harvest date.*—Peak harvest occurred on February December 21 in Tala, Mexico when plants were pruned the previous May. Dependent on timing of previous pruning.
*e. Mean date last pick.*—Last pick occurred on May 1 in Tala, Mexico when plants were pruned the previous May. Dependent on timing of previous pruning.
*f. Cluster density.*—Low.
*g. Berry cluster.*—Loose.
*h. Berries per cluster.*—Average of 3.
*i. Unripe fruit color.*—Pantone color Lettuce Green 13-0324, Damson 18-1725, Eggplant 19-2311 in Lowell, Oreg.
*j. Ripe berry color.*—Pantone colors Dapple Gray 16-3907, Blue Fog 15-4008, Deep Cobalt 19-3935 in Lowell, Oreg.
*k. Berry skin color after polishing.*—Pantone color Dark Navy 19-4013 with some Blue Fog 15-4008 in Oregon.
*l. Berry surface wax abundance.*—Heavy, rubs easily.
*m. Berry flesh color.*—Pantone colors Endive 13-0632 to Pastel Yellow 11-0616 in Lowell, Oreg.
*n. Berry weight.*—Average of 2.42 grams in Tala, Mexico over the course of the 2014-2015 harvest season, in comparison to an average of 1.16 grams for 'Biloxi'.
*o. Berry height from calyx to scar.*—Average of 13.11 mm.
*p. Berry diameter.*—Average of 17.41 mm.
*q. Calyx aperture.*—Average of 4.36 mm.
*r. Calyx depth.*—Average of 1.8 mm.
*s. Pedicel length.*—Average of 9.40 mm.
*t. Pedicel surface texture.*—Smooth.
*u. Berry detachment force.*—Medium.
*v. Berry shape.*—Oblate.
*w. Fruit stem scar.*—Small, dry.
*x. Berry flavor.*—Slightly tart, overall mild.
*y. Sweetness when ripe.*—Medium.
*z. Firmness when ripe.*—Good. (1) Acidity when ripe — medium. (2) Storage quality — good. (3) Suitability for mechanical harvesting — poor. (4) Self-fruitfulness — good. (5) Uses — commercial fruit production for the fresh market.

SEED

General:
*a. Seed abundance in fruit.*—Moderate in Lowell, Oreg. — average 18 seeds per berry.
*b. Seed color.*—Panton color Madder Brown 19-1331.
*c. Seed dry weight.*—3.4 mg for seed grown in Lowell, Oreg.
*d. Seed length.*—Average 1.89 mm.

COMPARISON BETWEEN PARENTAL AND COMMERCIAL CULTIVARS

| Denomination of similar variety | Characteristic for comparison | State of expression of similar variety | State of expression of candidate variety (FCM12-045) |
|---|---|---|---|
| ZF04-002 | Corolla shape | Urceolate | Cylindrical, narrow |
| FL95-138 | Color of new leaves | Pale yellowish green | Salmon or orange |
| ZF04-002 | Leaf glaucescence (wax) | Low | High |
| FL95-138 | Leaf glaucescence (wax) | Low | High |
| Biloxi | Leaf margin | Slightly serrate | Entire |
| Ventura | Plant vigor | High | Medium to low |

The invention claimed is:

1. A new and distinct variety of blueberry plant named 'FCM12-131' substantially as illustrated and described herein.

* * * * *